United States Patent [19]

Meybeck

[11] Patent Number: 5,643,598
[45] Date of Patent: Jul. 1, 1997

[54] METHOD OF SKIN CARE UTILIZING LIPOSOMES CONTAINING SCUTELLARIA EXTRACTS

[75] Inventor: Alain Meybeck, Courbevoie, France

[73] Assignee: LVMH Recherche, Colombes Cedex, France

[21] Appl. No.: 473,336

[22] Filed: Jun. 7, 1995

Related U.S. Application Data

[62] Division of Ser. No. 835,004, Feb. 12, 1992, Pat. No. 5,443,839, which is a continuation of Ser. No. 576,441, filed as PCT/FR89/00020 Jan. 23, 1989, abandoned.

Foreign Application Priority Data

Mar. 9, 1988 [FR] France .................... 88 03066

[51] Int. Cl.⁶ .................... A61K 9/127; A61K 7/00
[52] U.S. Cl. .................... 424/450; 424/401; 424/195.1; 514/844
[58] Field of Search .................... 424/450, 401, 424/195.1; 514/844

[56] References Cited

U.S. PATENT DOCUMENTS

| | | | |
|---|---|---|---|
| 4,235,871 | 11/1980 | Papahadjopoulos | 424/19 |
| 4,670,185 | 6/1987 | Fujiwara | 252/311 |
| 4,804,678 | 2/1989 | Augstein | 514/456 |
| 4,828,837 | 5/1981 | Uster | 424/450 |
| 4,917,951 | 4/1990 | Wallach | 428/402.2 |
| 4,931,284 | 6/1990 | Ekman | 514/963 |
| 4,997,649 | 3/1991 | Papaconstantin | 424/195.1 |

FOREIGN PATENT DOCUMENTS

| | | |
|---|---|---|
| 0224837 | 11/1986 | European Pat. Off. |
| 8500515 | 4/1985 | WIPO |

OTHER PUBLICATIONS

Patent Abstracts of Japan 10, 61–50918(A) 1986.
Patent Abstracts of Japan 4, 55–127209(A) 1980.
Chemical Abstracts, 93 36825 (1980).
Kubo et al J. Med. Plant Res. 43, 193 (1981).
Nikaido et al Chem. Pharm. Bull 36 (2) p. 654, Feb. 1988.
Merck Index. pp. 136, 137, 587, 1983.
Podhajcer Chem. Abstracts #368625 vol. 93 #5, 1980.

*Primary Examiner*—Gollamudi S. Kishore
*Attorney, Agent, or Firm*—Bryan Cave LLP

[57] ABSTRACT

The invention relates to a composition based on hydrated lipid lamellar phases or liposomes.

This composition is characterized in that said hydrated lipid lamellar phases or said liposomes contain at least in part an extract of Scutellaria, or at least one active substance isolated from such an extract or obtained by chemical synthesis, particularly wogonine, 2'-hydroxy-wogonine, baicaleine, neobaicaleine, oroxindine and baicaline.

This composition is useful for the preparation of cosmetic or pharmaceutical, particularly dermatological compositions, with anti-allergic, anti-inflammatory or anti-ageing activity.

11 Claims, 2 Drawing Sheets

METHOD OF SKIN CARE UTILIZING LIPOSOMES CONTAINING SCUTELLARIA EXTRACTS

RELATED U.S. APPLICATION DATA

Division of Ser. No. 07/835,004, filed Feb. 12, 1992 now U.S. Pat. No. 5,443,839, which is a continuation of Ser. No. 07/576,441, Sep. 7, 1990, filed as PCT/FR89/00020, Jan. 23, 1989, abandoned.

The present invention essentially relates to a composition based on hydrated lipid lamellar phases or liposomes containing an extract of Scutellaria, or at least one of its constituents, and a cosmetic or pharmaceutical, particularly dermatological composition, with anti-allergic, anti-inflammatory, anti-ageing activity, incorporating it.

The plant varieties of Scutellaria of the Labiatae family include without limitation *Scutellaria Baicalensis, Scutellaria Viscidula* or *Scutellaria Galericulata*.

The most well known extracts of Scuteliaria are extracts of roots of *Scutellaria Baicalensis Georgi* (*Scutellaria Radix*) also named "OGON" or even "OUGON".

Extracts of Ogon as defined hereinabove are widely described in the prior art for cosmetic, pharmaceutical and horticultural use.

Japanese Patent Application JP-57-209895 published under No. JP-A-59-101412 describes a cosmetic composition for hair protection containing an extract of Ogon (*Scutellaria Baicalensis* root).

Similarly, Japanese Patent Application JP-57-183419 published under No. JP-A-59-73509 describes a cosmetic composition containing Ogon in powder form at a rate of 0.005–2% by weight, or an extract thereof as an essential component, this composition presenting an excellent effect of improving dry skins, spots, wrinkles, etc. . . . . This Application specifies that the Ogon is constituted by dried roots of *Scutellaria Baicalensis Georgi* or of related plants.

The use of extract of *Scutellaria Radix* for preparing a cosmetic composition avoiding the formation of spots on the skin is also described in Japanese Patent Application JP-59-241641 published under No. JP-A-61-122209, in mixture with other active components.

The use of Scutellaria as one of the components of a multi-component extract for the formation of a skin reactivator is described in Japanese Patent Application JP-54-172382 published under No. JP-A-56-92821.

Japanese Patent Application JP-54-34771 published under No. JP-A-55-127309 also describes a cosmetic composition comprising an extract of *Scutellaria Baicalensis Georgi* for the prevention of hardness, sun burns and inflammation of the skin. The cosmetic formulation may be used in the form of lotion, cream, emulsion, cleaning cream and soap.

Pharmaceutical composition containing Ogon are described respectively in: JP-A-62-26229 (*Scutellaria Radix*, agent for promoting differentiation of the nervous cells); JP-A-61-167623 (Ougon, root of *Scutellaria Baicalensis*, agent for inhibiting coagulation of the platelets); JP-A-61-161219 (*Scutellaria Baicalensis Georgi* or *Scutellaria Viscidula Buxge*, treatment of atopical dermatites); JP-A-61-109733 (Ougon, root of *Scutellaria Baicalensis*, carcinostatic agent); JP-A-61-263923 (2-interleucine inductor of low toxicity containing, in a mixture of herb extract, an extract of Ogon); JP-A-58-121218 (composition for the control of tooth decay comprising, inter alia, an extract of *Scutellaria Baicalensis*; GB-A-10-96708 (anti-narcotic drug containing, inter alia, roots of *Scutellaria Baicalensis Georgi* (5%)); jP-A-62-033125 (drug improving the anti-cancerous effect of Tegafur contaning, inter alia, roots of Scutellaria in powder form).

Extracts of Ogon have also been used in agriculture for the production of an agent activating plant growth (JP-A-61-115009); as fungicide (JP-A-56-022709); or as plant disease control agent (JP-A-62-129209).

Likewise, certain active agents have been extracted from Ogon, such as baicaline as constituent for the treatment of allergic diseases (cf. JP-A-61-50921), baicaline or baicaleine also as anti-allergic agent (JP-A-61-50918), as well as Planta Medica, J. Medici. Plant Research 1981, vol. 43, pages 194–201. As deodorant component, the baicaleine or baicaline has also been used (JP-A-61-268259); derivatives of baicaleine in the form of salt and of demi-ester as anti-inflammatory or anti-asthmatic agent are described in JP-A-70-25716=U.S. Pat. No. 3,549,662. The use of wogonine and of baicaline is described in JP-A-48-68717 for the treatment of arteriosclerosis, apoplexy and hypercholesterolaemia.

The use of baicaline, of wogonine, etc. . . . . , is described for the preparation of anthocyanic pigment in JP-A-55-13711.

Finally, the use of Scutellaria in cosmetic compositions for retaining water in the skin is described in JP-A-60-258104.

It may thus be ascertained that the use of Scutellaria and in particular of Ogon extract, or of various constituents thereof, is widely described in the cosmetic or pharmaceutical fields.

Furthermore, the use of hydrated lipid lamellar phases or liposomes in pharmaceutical compositions or cosmetic compositions, in which various active ingredients are incorporated, is already known (FR-A-2540 381).

It has now been quite surprizingly and unexpectedly discovered that the incorporation of the above-mentioned extract of Scutellaria, in particular of Ogon extract, or of active substance having been able to be isolated from such an extract of Ogon or obtained by chemical synthesis, selected in particular from: 2',5,7-trihydroxy-8-methoxy-flavone (or 2'-hydroxy-wogonine), 2',5-dihydroxy-6,6',7,8-tetra-methoxy-flavone (or skullcap flavone II or neobaicaleine), 2',5,5',7-tetrahydroxy-6',8-dimethoxy-flavone, 5-hydroxy-8-methoxy-flavone-7-O-D-glucuronide (or wogonin-7-O-D-glucuronide or oroxindine), 5-hydroxy-7,8-dimethoxy-flavone (or 7-O-methyl-wogonine), 5,7-dihydroxy-6-methoxy-flavone (or oroxyline A or 6-O-methyl-baicaleine), 4',5,7-trihydroxy-8-methoxy-flavone (or 4'-hydroxy-wogonine), 2',5,6'-trihydroxy-7,8-dimethoxy-flavone, 5,7,8-trihydroxy-flavone (or nor-wogonine), 5,6,7-trihydroxy-flavone (or baicaleine), 5,8-dihydroxy-6,7-dimethoxy-flavone; 2',3,5,6',7-pentahydroxy-flavone, 4',5,6-trihydroxy-flavone-7-O-D-glucuronide (or 4'-hydroxy-baicaline, 5,6-dihydroxy-flavone-7-O-D-glucuronic methyl ester acid (or baicaline methyl ester), 2',5,7-trihydroxy-flavone (2'-hydroxy chrysine), 5,7-dihydroxy-8-methoxy-flavone (or wogonine), 2',5,7-trihydroxy-6',8-dimethoxyflavone (or 2'-hydroxy-6'-methoxy-wogonine), 4',5,6,7-tetrahydroxy-flavone (or 4'-hydroxy-baicaleine), 5,6-dihydroxy-flavone-7-O-D-glucoside (baicaleine-7-O-D-glucoside), 5-hydroxy-4',6,7-trimethoxy-flavone (or salvigenine), 5-hydroxy-6-methoxy-flavone-7-O-D-glucuronide (or oroxyline A-7-O-D-glucuronide), 5,6-dihydroxy-flavone-7-O-D-glucuronide (or baicaline), 5-hydroxy-6-methoxy-flavone-7-O-D-glucuronic methyl ester acid (or oroxindine methyl ester), 5,7- dihydroxyflavone (or chrysine), and preferably from: wogonine, 2'-hydroxy-wogonine, baicaleine, neobaicaleine, oroxindine, baicaline, at least partly in a hydrated lipid lamellar phase or in liposomes, provoked a more intensive activity of this extract of these substances. This concerns all the activities known for the extracts of Ogon or the substances isolated from such extracts such as the substances mentioned above. An even more radical improvement in activity has been observed in the anti-inflammatory, anti-allergic activey and anti-ageing activity.

An effect of synergy may thus to some extent be deduced therefrom for incorporations of extract of Scutellaria, in particular of Ogon extract or active substances isolated from such extracts, such as the substances mentioned above, in hydrated lipid lamellar phases or in liposomes.

The present invention thus has for its object to solve the new technical problem consisting in supplying a novel formulation of ektract of Scutellaria, in particular of Ogon extract, or of any active substance isolated from such an extract or reconstituted by chemical synthesis, making it possible to potentialize their effectiveness in order to allow use thereof in cosmetic or pharmaceutical, particularly dermatological compositions, with anti-inflammatory, anti-allergic or anti-ageing activity.

The present invention solves this new technical problem for the first time, in satisfactory manner.

Thus, according to a first aspect, the present invention furnishes a composition based on hydrated lipid lamellar phases or liposomes, characterized in that said hydrated lipid lamellar phases or said liposomes contain at least in part an extract of Scutellaria, or at least an active substance isolated from such an extract or obtained by chemical synthesis, in particular from: 2',5,7-trihydroxy-8-methoxyflavone (or 2'-hydroxy-wogonine), 2',5-dihydroxy-6,6',7,8-tetramethoxy-flavone (or skullcap flavone IIor neobaicaleine), 2',5,5',7-tetrahydroxy-6',8-dimethoxy-flavone, 5-hydroxy-8-methoxy-flavone-7-O-D-glucuronide (or wogonin-7-O-D-glucuronide or oroxindine), 5-hydroxy-7,8-dimethoxy-flavone (or 7-O-methyl-wogonine), 5,7-dihydroxy-6-methoxy-flavone (or oroxyline A or 6-O-methyl-baicaleine), 4',5,7-trihydroxy-8-methoxy-flavone (or 4'-hydroxy-wogonine),2',5,6'-trihydroxy-7,8-dimethoxy-flavone, 5,7,8-trihydroxy-flavone (or norwogonine), 5,6,7-trihydroxy-flavone (or baisaleine), 5,8-dihydroxy-6,7-dimethoxy-flavone, 2',3,5,6',7-pentahydroxy-flavone, 4',5,6-trihydroxy-flavone-7-O-D-glucuronide (or 4'-hydroxy-baicaline), 5,6-dihydroxy-flavone-7-O-D-glucuronic methyl ester acid (or baicaline methyl ester), 2',5,7-trihydroxy-flavone (2'-hydroxy chrysine), 5,7-dihydroxy-8-methoxy-flavone (or wogonine), 2',5,7trihydroxy-6',8-dimethoxy-flavone (or 2'-hydroxy-6'-methoxy-wogonine), 4',5,6,7-tetrahydroxy-flavone (or 4'-hydroxy-baicaleine), 5,6-dihydroxy-flavone-7-O-D-glucoside (baicaleine-7-O-D-glucoside), 5-hydroxy-4',6,7-trimethoxy-flavone (or salvigenine), 5-hydroxy-6-methoxy-flavone-7-O-D-glucuronide (or oroxyline A-7-O-D-glucuronide), 5,6-dihydroxy-flavone-7-O-D-glucuronide (or baicaline), 5-hydroxy-6-methoxy-flavone-7-O-D-glucuronic methyl ester acid (or oroxindine methyl ester), 5,7-dihydroxy-flavone (or chrysine).

For a precise description of these isolated substances, reference may be made to the description of the prior art, particularly to Planta Medica, Journal of Medicinal Plant Research (1981), vol. 43, pages 194–201, likewise in Chem. Pharm. Bull., (1984), vol. 32, pages 5051–5054, or Chem. Pharm. Bull. (1988), vol. 36, No. 2, pages 654–661. The chemical structures of eight flavonoid compounds isolated from *Scutellaria Baicalensis Georgi* were presented in Plants Medica at pages 195 and 197 and are set forth below:

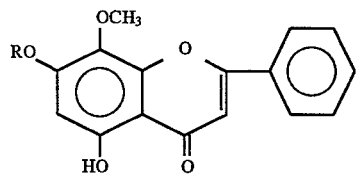

I: Wagonin R = H
VII: R = glucuronic acid

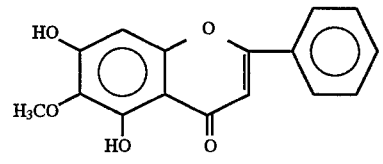

II: Oroxylin A

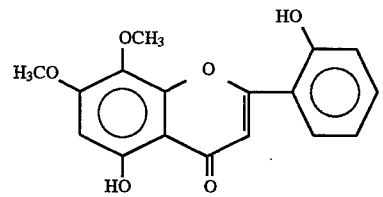

III: Skullcapflavone I

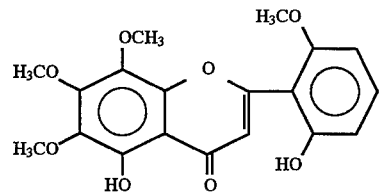

IV: Skullcapflavone II

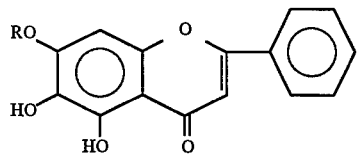

V: Baicalein R = H
VI: Baicalin R = glucuronic acid

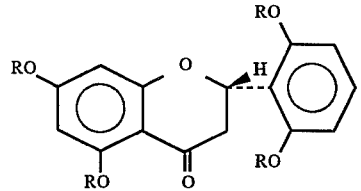

VIII: 2(S),2',5,6,7-tetrahydroxyflavanone

The chemical properties of wogonin (I), skullcapflavone II (IV), baicalein (V), and 2(S),2',5,6,7-tetrahydroxyflavanone (VIII) are described on page 195 of Plants Medica as follows:

Wogonin (I)

Yellow needles from n-hexane: EtOAc, mp. 202°–203°, [lit. mp. 203°] [1]. In the IR and PMR spectra data, it was identical with authentic sample of woginin. Yield 25 g.

Skullcapflavone II (IV)

Yellow prisms from EtOAc, mp. 180° [Lit. mp. 180°–181°][1]. MG+HCl: Orange yellow. PMR (in DMSO-$d_6$) δppm: 3.76, 3.80, 3.82, 4.00 (3H, each singlet, —OCH$_3$), 6.22 (1H, singlet, C$_3$-H), 6.56 (2H, doublet, J=8.0 Hz, C$_3$-H and C$_5$-H), 7.24 (1H, triplet, J=8.0 Hz, C$_4$-H), 10.0 (1H, broad singlet, C$_2$-OH), 12.67 (1H, singlet, C$_5$-OH). IR $v_{max}^{nujol}$ cm$^{-1}$: 3200–3100 (OH), 1650 (C=O), 1600, 1560 (aromatic ring). UV $\lambda_{max}^{EtOH}$ nm (log ε): 270 (4.46). From the PMR spectra data it was identical with that reported for skullcapflavone II [1]. Yield 500 mg.

Baicalein (V)

Yellow prisms from CHCl$_3$: MeOH, mp. 263° (decomp.) [Lit. mp. 265°] [2]. From the IR and PMR spectra data it was identical with an authentic sample of baicalein. Yield 53 g.

Baicalin (VI)

Yellow crystalline powder from MeOH, mp. 220° (decomp.) [Lit. mp. 223°] [2]. From the IR and PMR spectra data it was identical with an authentic sample of baicalin and the melting point showed no depression on admixture with an authentic sample. Baicalin, which was required for comparison of antibacterial effects, was isolated from the MeOH extract of roots of S. baicalensis.

2(S)2', 5,6',7-tetrahydroxyflavanone (VIII)

Colorless prisms from n-hexane: EtOAc, mp. 240° (decomp.), Mg+HCl: Orange yellow, 1% Ce(SO$_4$)$_2$ (10% H$_2$SO$_4$): Orange, FeCl$_3$ reagent: dark green [α$_D^{20°}$+6.13° (C=1.012, MeOH). MS m/e 288 (M+). Anal. Calcd. for C$_{15}$H$_{12}$O$_6$: C, 62.50; H, 4.20; mol. wt., 288.25. Found: C, 62.54; H, 4.22. IR $v_{max}^{nujol}$ cm$^{-1}$:3450, 3200 (OH), 1640 (chelated C=O), 1610, 1517 (aromatic ring) UV $\lambda_{max}^{EtOH}$ nm (log ε): 289 (4.21); UV $\lambda_{max}^{EtOH(AlCl')}$ nm: 312; UV $\lambda_{max}^{EtOH(AcONa)}$ nm: 327.

PMR (in DMSO-$d_6$) δppm: 2.35 (1H, doublet, J=4.0 Hz, C$_3$-H), 340 (1H, quartet, J=14.0 Hz, 17.0 Hz, C$_3$-H), 5.83, 5.87 (1H, each doublet, J=2.5 Hz, aromatic H), 5,84 (1H, quartet, J=14.0 Hz, 4.0 Hz, C$_2$-H), 6.32 (2H, doublet, J=9.0 Hz, aromatic H), 6.98 (1H, triplet, J=9.0 Hz, aromatic H), 9.48 (2H, singlet, OH×2, disappeared by the addition of D$_2$O), 12.24 (1H, singlet, OH, disappeared by the addition of D$_2$O). CD (C=0.126, MeOH) [θ]$^{25°}$(nm): −29000 (284), +7800 (306), +9400 (327). Yield 2.3 g.

According to an advantageous embodiment of this composition, said active substance is selected from the group constituted by wogonine, 2'-hydroxy-wogonine, baicaleine, neobaicaleine, oroxindine and baicaline.

According to a particular feature of this composition, the latter contains an extract of Scutellaria obtained by an extraction by solvent, preferably selected from the group consisting of a polar solvent, in particular an alcohol, water-alcohol or ethereal solution; of an apolar organic solvent such as n-hexane benzene or a combination of the two.

According to a variant embodiment, an extraction is firstly effected with a polar organic solvent, followed by an extraction with an apolar organic solvent, in order to collect the fraction insoluble in the apolar solvent, as described in Planta Medica, Journal of Medicinal Plant Research, 1981, Vol. 43, pages 194–201. The extraction procedure is described in Plants Medica at pages 194–200 as follows:

The ether extract of roots of S. baicalensis was extracted with n-hexane. The n-hexane insoluble fraction, having anti-bacterial activity, was chromatographed on a column over silica gel by the procedure as shown in FIG. 2, yielding the antibacterial compound (VIII).

Melting points were determined on a Yamato Model MP-21 capillary and were uncorrected. IR spectra were measured on a Shimazu IR-400. UV spectra were obtained on a Shimazu MPS-5000. PMR spectra were recorded in DMSO-$d_6$, CDCl$_3$ and D$_2$O on a Hitachi R-22 (90 MHz). TMS was used as an internal standard and chemical shifts are reported in delta (ppm and Hz). Column chromatography was carried out using silica gel 60 (70–230 mesh, ASTM, Merck) as adsorbent. Pre-coated TLC plates silica gel 60F$_{254}$ (Merck) were used for TLC.

Extraction and Isolation of the Antibacterial Components

The crushed drug (10 kg) was extracted with 4×20 l of ether at room temperature. The ether solution was concentrated to give a yellowish powder (140 g), which by treatment with n-hexane, was divided into soluble (40 g) and insoluble (100 g) fractions. The n-hexane insoluble extract (100 g) was chromatographed on a column over silica gel to afford the compound as shown in FIG. 2.

According to a variant embodiment of this composition, the latter is characterized in that the above-mentioned extract of Scutellaria alone or in mixture with other compatible active substances, is introduced into the lipid phase of the hydrated lipid lamellar phases or liposomes.

According to another variant embodiment of this composition, the latter is characterized in that the above-mentioned extract of Scutellaria alone or in mixture with other compatible active substances, is introduced into the aqueous phase of the hydrated lipid lamellar phases or liposomes.

According to a particular embodiment, the extract of Scutellaria is an extract selected from the group consisting of Scutellaria Baicalensis, of Scutellaria Viscidula, or of Scutellaria Galericulata. According to an advantageous embodiment, the above-mentioned extract of Scutellaria is an extract of roots of Scutellaria Baicalensis Georgi, also called extract of Ogon.

According to a second aspect, the present invention also relates to a cosmetic or pharmaceutical, particularly dermatological composition, with anti-inflammatory, anti-allergic or anti-ageing activity, characterized in that it comprises a composition based on hydrated lipid lamellar phases or liposomes, as defined hereinbefore.

The proportion by weight of the dry extract of Scutellaria or of any active substance obtained from such an extract or by chemical synthesis is included between 0.0001 and 2% relatively to the total weight of the composition it is preferably included between 0.001 and 0.4% relatively to the total weight of the composition.

A crude extract of Ogon available on the market, particularly in 50% water-alcohol solution, may also be used in more practical manner, which extract may be used at a rate of 0.005 to 50%, and even better between 0.05 and 20% by weight with respect to the total weight of the composition.

Similarly, this pharmaceutical, particularly dermatological, or cosmetic composition may, according to a first variant, be characterized in that the above-mentioned extract of Scutellaria, or any active substance extracted therefrom, alone or mixed with other compatible active substances, is introduced in the lipid phase of the hydrated lipid lamellar phases or liposomes, whilst, according to another variant, such introduction may be effected in the aqueous phase of the hydrated lipid lamellar phases or liposomes.

In the present description and Claims, the term "lipid" in the expression "lipid lamellar phase" covers all the substances comprising a so-called fatty carbon chain, generally more than 5 carbon atoms.

According to the invention, amphiphilic lipids are used, i.e. constituted by molecules presenting a hydrophilic group which may equally well be ionic or non-ionic and a lipophilic group, such amphiphilic lipids being capable of forming lipid lamellar phases in the presence of an aqueous phase. The following may be cited in particular among these lipids: phospholipids, phosphoaminolipids, glycolipids, polyoxyethylene fatty alcohols, possibly polyoxyethylene polyol esters. Such substances are for example constituted by an egg or soya lecithin, a phosphatidylserine, a sphyngomyelin, a cerebroside or an oxyethylene polyglycerol stereate.

Other purposes, characteristics and advantages of the invention will clearly appear on reading the following explicative description made with reference to several Examples of the invention given simply by way of illustration and which could therefore in no way limit the scope of the invention. In the Examples, the percentages are given by weight unless indicated to the contrary.

EXAMPLE 1

Figure 1:
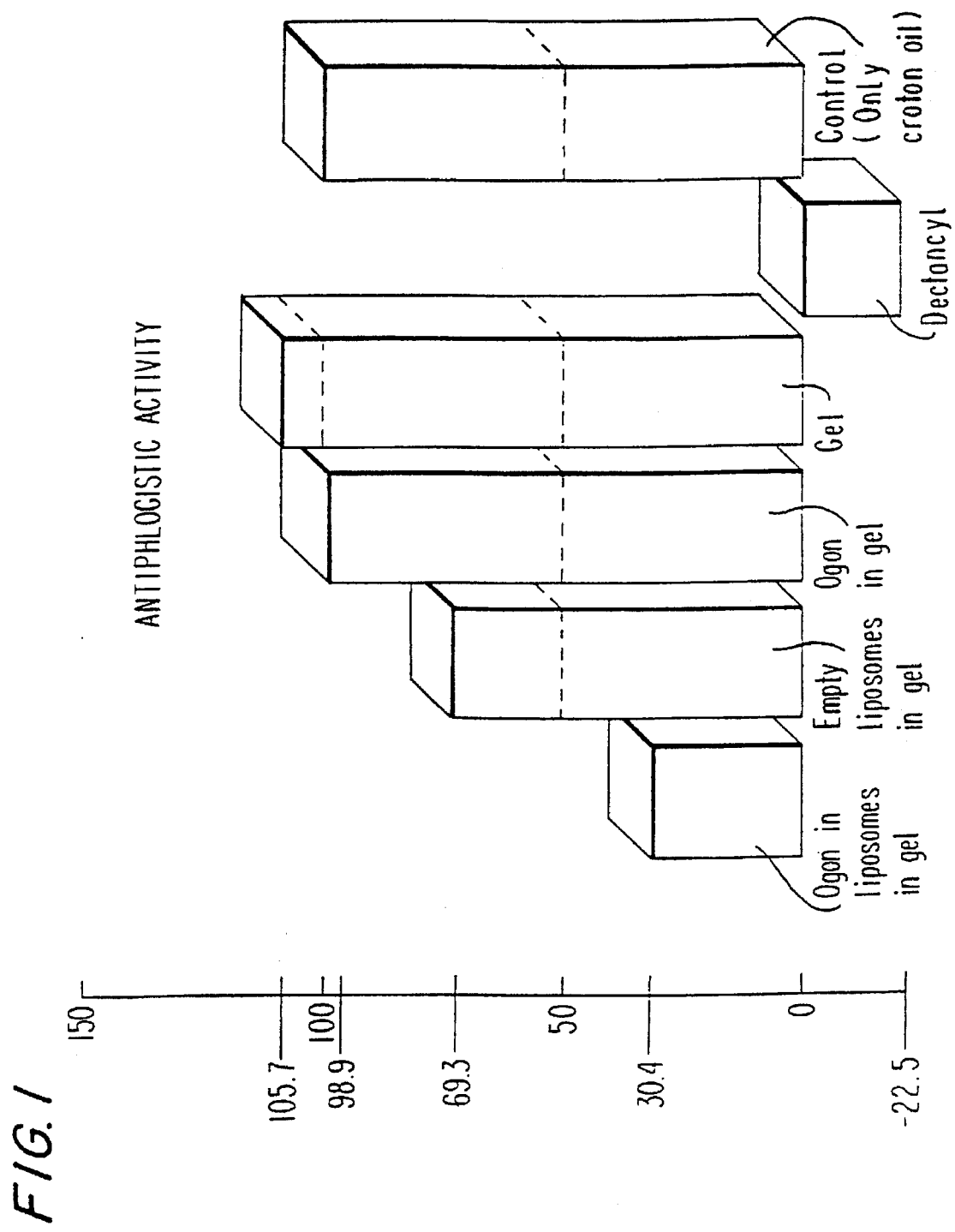
FIG. 1 is a histogram of antiphlogistic activity based on the results of Table II. The height of the bars represent the magnitude of the inflammatory reaction provoked by the croton oil.
Figure 2:
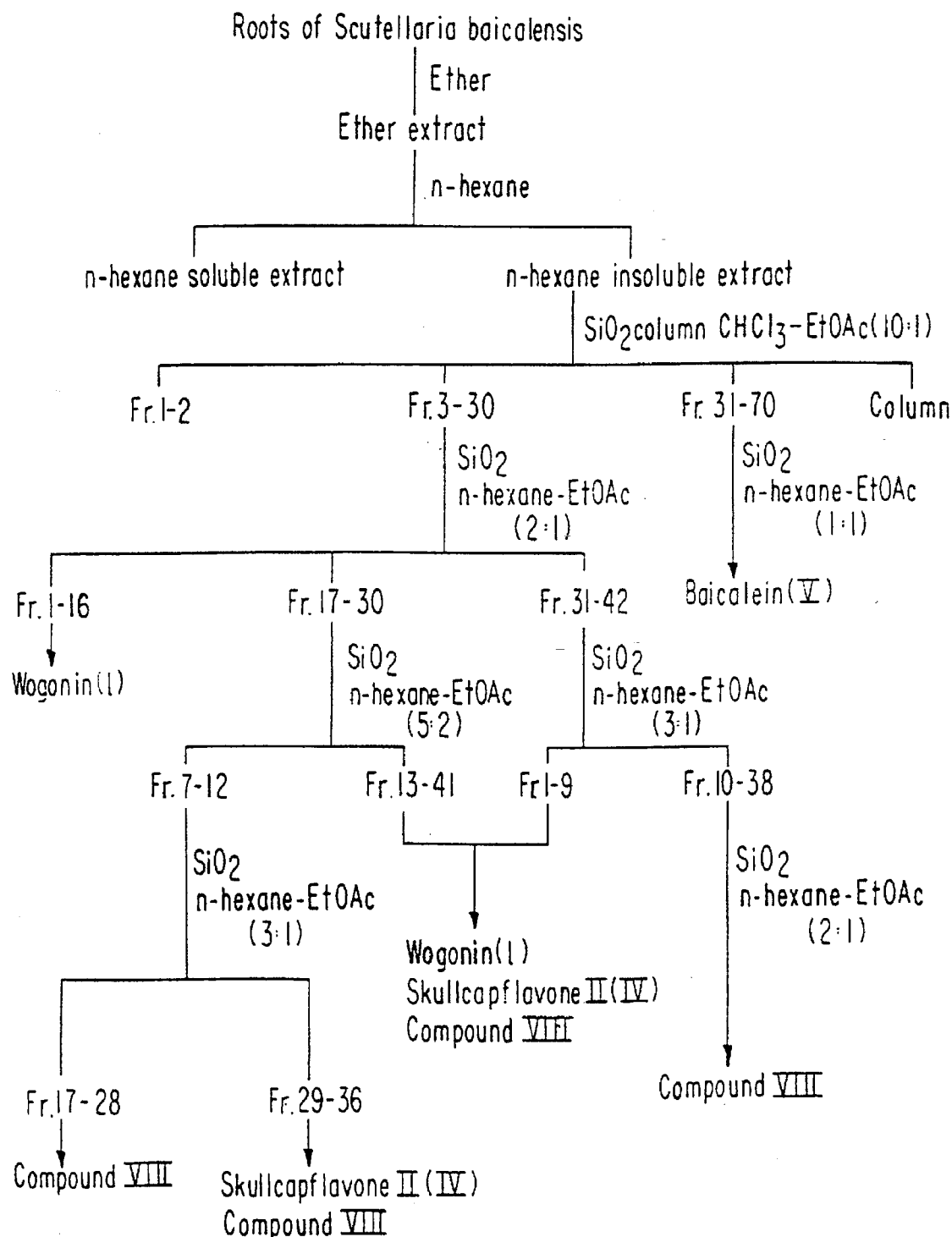
FIG. 2 is a flow chart of the isolation of antibacterial substance (VIII), wogonin (I), Skullcapflavone II (IV) and Baicalein (V) from the roots of *Scutellaria Baicalensis*.

A—Preparation of a Composition in the Form of an Advantageously Homogenized Liposome Suspension The extract of Ogon used is an extract of Ogon obtained from *Scutellaria Baicalensis Georgi* root marketed by the Japanese firm Ichimaru Pharcos Co. Limited, constituted here by batch No. IT134, called "Woogon extract-E", and which is in the form of a 50% vol/vol water-alcohol solution in ethanol, having a density of 0.931, a residue content after evaporation of 1.38% by weight/volume, a content of baicaline of 0.16% by weight/volume and a very low content of baicaleine.

This extract of Ogon (also called Ougon or Woogon in the art) may be evaporated to dryness, or, in more practical manner, used as such for preparing a composition in the form of liposome suspension, in the following manner:
Composition

| | |
|---|---|
| extract of Ogon (Woogon extract No. IT134, 50% water-alcohol solution in ethanol) | 0.5 g |
| bidistilled water | 47.5 g |
| lecithin of soya | 2.0 g |

This composition prepared the following manner:

The Ogon extract is firstly added in the bi-distilled water, with stirring, then the soya lecithin is dispersed in this aqueous solution.

This solution is homogenized with continued stirring for about 2 hrs.

Homogeneization is preferably carried out by ultrasounds, by effecting a sonication for 10 mins. at 100 W, which makes it possible to obtain a mean liposome dimension of the order of 106.7 nm ±0.5 nm.

Instead of an ultra-sound homogeneization, a homogeneization under pressure may be carried out, for example in accordance with the process described in FR-A-2 534 487.

It will be observed that various dilutions may be made by modifying the quantity of extract added at the start or by increasing the volume of the solution of dispersion, which constitutes an easy process for preparing various concentrations of extract.

In the absence of a dilution, 50 g of homogenized suspension, corresponding to about 50 ml, are obtained after this step A.

B—Preparation of a Composition of Homogenized Liposomes in the Form of Gel

This homogenized suspension may be gelled by mixture with a gel, such as a vinyl polymer gel, in particular marketed under the Trademark Carbopol® 940.

To prepare this gel in conventional manner, 0.5 g of Carbopol® 940 may for example be dispersed in 50 g of water in the presence of a conservation agent and a conventional chelating agent, then, after swelling, triethanolamine may preferably be used for neutralizing to pH 7.5.

In this way, 50 ml of said gel are added to the 50 g or millilitres of homogenized suspension obtained in step A hereinabove, in order to obtain a total volume of about 100 ml.

In this gelled composition, the concentration of dry extract of Ogon is about 0.069% and the concentration of lecithin is 2%.

This composition thus gelled, referenced CI.1, will be used in the activity trials given hereinbelow in the present description.

EXAMPLE 2

Composition of Liposomes Containing Extract of Ogon in the Lipid, Possibly Gelled Phase 1.0 g of Ogon extract of Example 1 is taken, which is dissolved in 50 $cm^3$ of chloroform.

The substance is evaporated to dryness under reduced pressure in a rotary evaporator at a temperature of the order of 56° C.

The residue deposited on the wall of the rotary flask is taken up with 10 ml of methanol.

2 g of soya lecithin as well as 50 ml of chloroform are added.

The whole solution is evaporated under reduced pressure in the same rotary flask at a temperature of about 56° C. in order to obtain a film which is deposited on the wall of the rotary flask.

This film is then taken up with 48.0 g of water.

Stirring is effected for 3 hrs. with the aid of a magnetic stirrer in order to obtain a suspension of liposomes containing the extract of Ogon at least in part in the lipid phase.

The liposomes may be homogenized by sonication for 10 mins. at 100 W in an ice bath in order to obtain a suspension of homogenized liposomes.

This solution may possibly be gelled in the same manner as in Example 1, in order to obtain a gelled composition having a concentration of dry extract of Ogon of about 0.138% by weight/volume and a concentration of lecithin of 2%.

EXAMPLE 3

Baicaleine in Liposomes

The procedure is the same as in Example 2, except that 0.1 g of baicaleine is used in place of the extract of Ogon.

EXAMPLE 4

Comparative Compositions

4-A 0.5 g of the extract of Ogon of Example 1 is taken which is added to 49.5 g of bidistilled water and a mixture is made with stirring for some minutes.

5 g of 1% Carbopol® 940 gel prepared as described in Example 1B, are then added so as to obtain a gelled composition for comparison referenced C.P. No. 1.

4-B

A control comparative composition referenced C.P No. 2 is also prepared by mixing 50 g of bidistilled water and 50 g of 1% Carbopol® 940 gel prepared as described in Example 1.

4-C Another liposomal comparative composition is prepared in the manner indicated in Example 1, without active substance, i.e. no extract of Ogon is employed. This composition is therefore formed by 2 g of soya lecithin, 47.5 g of bidistilled water, then the suspension which was homogenized with ultrasounds as indicated in Example 1A is gelled as indicated in Example 1B in order to furnish a comparative composition referenced C.P No. 3.

EXAMPLE 5

Demonstration of the Anti-Allergic and Anti-Inflammatory Activity of the Compositions According to the Invention The use of the composition of Example 1 as pharmaceutical, particularly dermatological, or cosmetic composition is checked by carrying out the following in vivo experiments:

1 —Demonstration of the Anti-Allergic Activity

The anti-allergic activity is tested by the DNCB (chloro-1-dinitro-2,4-benzene) test in the guinea pig.

To that end, 5 batches of 10 guinea pigs having substantially the same weight and presenting no detectable sign of allergy, are formed.

The 50 guinea pigs are sensitized with DNCB by an intradermic injection of DNCB at 0.2% by weight. One week afterwards, they receive a topical application of the same solution of DNCB at 0.2%.

The guinea pigs are then left to rest for 12 days.

After this period, the allergic reaction is again provoked by a fresh patch application of a solution of DNCB at 0.02%.

In order to test the anti-allergic activity of the composition according to the invention of Example No. 1 (batch No. 1) in comparison with the other comparative compositions indicated hereinafter (batch No. 2 to batch No. 5), the guinea pigs had received in application, 1 hour before the patch application, respectively:

for batch No. 1: 1 ml of extract of Ogon in liposome (CI1 of Example 1) (Ogon in liposomes in gel)

for batch No. 2: 1 ml of extradt of Ogon at 0.5% in gel (CP No. 1 of Example 4-A) (Ogon in gel)

for batch No. 3: 1 ml of gel (C.P No. 2 of Example 4-B) (gel)

for batch No. 4: 1 ml of "empty"liposomes in gel (C.P No. 3 of Example 4-C)

for batch No. 5: no application (control batch).

The intensity of the allergic reaction of the animals is noted from 0 to 5, the mark 5 being attributed to the most intense reaction observed.

Table I hereinbelow indicates the number of animals for each mark attributed.

TABLE I

| | 0 | 1 | 2 | 3 | 4 | 5 | TOTAL |
|---|---|---|---|---|---|---|---|
| 1:C.I1:ogon in liposomes in gel | 1 | 5 | 2 | 1 | 1 | — | 16 |
| 2:CP1:ogon in gel | — | 4 | 2 | 1 | 3 | — | 23 |
| 3:CP2:gel | 1 | 4 | 1 | 2 | 1 | 1 | 21 |
| 4:CP3:"empty" liposomes in gel | 2 | 2 | 2 | 2 | 2 | — | 20 |
| 5:control | — | — | — | 2 | 6 | 2 | 40 |

The results shown in Table I very clearly show that the allergic reactions are on average much less intense in the guinea pigs previously treated with the suspension of liposomes containing the extract of Ogon (batch No. 1), with respect to those observed in the animals of batches No. 2 to No. 5 receiving compositions taken by way of comparison (batch No. 2 to batch No. 4) or without any application (batch No. 5).

Moreover, it may also be observed that the extract of Ogon appears clearly more active in liposomes with respect to the free form in gel (batch No. 2).

This test therefore incontestably demonstrates the intense anti-allergic activity obtained by the incorporation of Ogon extract in hydrated lipid lameliar phases or liposomes made according to the invention.

2 —Demonstration of the Anti-Inflammatory Activity

The anti-inflammatory activity of the composition according to the invention is demonstrated by a croton oil test, made in accordance with the TONELLI method in the Journal Endocrinology, 1965, vol. 77, pages 624–634, made on the albino mouse in accordance with the following procedure:

The mice are distributed in seven batches of 8 mice, each batch being treated with a given product:

Batch No. 1 is treated with Ogon in liposomes,

Batch No. 2 is treated with empty liposomes in gel,

Batch No. 3 is treated with Ogon in gel,

Batch No. 4 is treated with gel alone,

Batch No. 5 is treated with Dectancyl,

Batch No. 6 is a control batch on which only croton oil is applied,

Batch No. 7 is another control batch which does not undergo any application, therefore without croton oil.

0.1 ml of the product to be tested is applied on the right ear 3 hrs., 2 hrs. and 1 hr. before the application of 0.05 ml of croton oil at 0.2% in acetone.

In order to avoid artifact phenomena at the level of absorption of the products, the oily excipients are proscribed in this study.

5½ hrs. later, the animals are sacrificed.

The treated ear is taken and weighed on precision scales (mettler).

The average of the weights is effected for each batch.

The average of the control weights will then be subtracted from the results obtained in the other batches, in order to obtain the values of increase in the weights of ears, with respect to the normal animals.

The percentage of protection of the tested products is then made by bringing the croton oil batch to 100%.

Table II gives the individual results.

Table III presents the statistical analysis by t of Student.

The results of Table II are shown in the form of a histogram in accompanying FIG. 1; the height of the bars represents the magnitude of the inflammatory reaction provoked by the croton oil applied in accordance with the procedure indicated hereinbefore.

It may be observed from these results of tests that the oedema provoked by croton oil (measured by weighing the ear) is not sfgnificantly reduced by the products applied, except for the extract of Ogon incorporated in liposomes in accordance with the present invention, and Dectancyl.

The activity of Dectancyl is significantly greater than the activity of the other products.

The extract of Ogon in gel, as well as the gel alone or the "empty" liposomes in gel, contributes no anti-phlogistic activity.

In addition, it may be observed that the extract of Ogon in liposomes according to the invention contributes an anti-phlogistic activity of 69.6%, which is remarkable and completely unexpected for a man skilled in the art.

TABLE II

| | Composition tested | | | | | | |
|---|---|---|---|---|---|---|---|
| | Ogon in liposomes (ex. 1, CI1) | Empty liposomes in gel (ex. 3-C) (CP3) | Ogon in gel (CP1) (ex. 3-A) | Gel alone (ex. 3-B) (CP2) | Dectancyl | Control (only croton oil) | Control (without croton oil) |
| 1 | 138 | 161 | 209 | 278 | 121 | 183 | 134 |
| 2 | 147 | 167 | 194 | 195 | 126 | 192 | 140 |
| 3 | 146 | 255 | 187 | 190 | 123 | 224 | 130 |
| 4 | 160 | 190 | 210 | 240 | 121 | 170 | 122 |
| 5 | 157 | 166 | 208 | 172 | 100 | 188 | 140 |
| 6 | 165 | 172 | 214 | 202 | 108 | 216 | 135 |
| 7 | 167 | 175 | 190 | 185 | 133 | 200 | 133 |
| 8 | 156 | 160 | 194 | 181 | | 238 | 138 |
| AVERAGE | 154.5 | 180.7 | 200.7 | 205.3 | 118.8 | 201.4 | 134 |
| STANDARD DEVIATION | 10.04 | 31.4 | 10.5 | 35.7 | 11.2 | 22.8 | 5.9 |
| AVERAGE PRODUCT MINUS AVERAGE CONTROL | 20.5 | 46.7 | 66.7 | 71.3 | −15.2 | 67.4 | |
| STANDARD DEVIATION | 15.9 | 36.3 | 16.4 | 41.6 | 17.1 | 28.7 | |
| HC brought to 100% | 30.4 | 69.3 | 98.9 | 105.7 | −22.5 | 100 | |
| PROTECTION | 69.6% | 30.7% | 1.1% | −5.7% | 122.5 | | |

TABLE III

| | OGON IN LIPOSOMES GEL (Ex. 1)(CI1) | EMPTY LIPOSOMES IN GEL (Ex. 3-C)(CP3) | OGON IN GEL (Ex. 3-A)(CP1) | GEL ALONE (Ex. 3-B)(CP2) | DECTANCYL | CONTROL (without croton oil) |
|---|---|---|---|---|---|---|
| OGON IN LIPOSOMES IN GEL (Ex. 1)(CI1) | | >* | >*** | >** | >*** | >*** |
| EMPTY LIPOSOMES IN GEL (Ex. 3-C)(CP3) | | | NS | NS | >*** | NS |
| OGON IN GEL (Ex. 3-A)(CP1) | | | | NS | >*** | NS |
| GEL ALONE (Ex. 3-B)(CP2) | | | | | >*** | NS |
| DECTANCYL | | | | | | >*** | t = 2,19
5% = 2,14
* = 5%
** = 1%
*** = 0,1%

Various examples of dermatological, dermocosmetic compositions are given hereinafter:

EXAMPLE 6

Cream for Sensitive Skins

A mixture of suspension of liposomes containing Ogon with an oil-in-water type emulsion is made in the following proportions:

| | |
|---|---|
| Composition of liposomes prepared in accordance with Example 1 with 0.2% dry extract of Ogon | 25 g |
| Emulsified oil-in-water excipient | qsp 100 |

A daily or twice-daily application is made in cold, dry weather.

EXAMPLE 7

Cream for Care Around the Eyes

A mixture of suspension of liposomes containing Ogon with an oil-in-water type emulsion is made in the following proportions:

| | |
|---|---|
| Composition of liposomes prepared in accordance with Example 2 with 0.15% of dry extract of Ogon | 30 g |
| Emulsified oil-in-water excipient | qsp 100 |

A daily application is made on the lower and upper eyelids.

EXAMPLE 8

Sun Milk

A mixture of suspension of liposomes containing Ogon with an oil-in-water type emulsion is made in the following proportions:

| | |
|---|---|
| Composition of liposomes prepared in accordance with Example 2 with 0.15% dry extract of Ogon | 30 g |
| Emulsified oil-in-water excipient laden with solar filters | qsp 100 |

EXAMPLE 9

Protective Gel for Skins Subject to Allergies

| | |
|---|---|
| Composition of liposomes prepared in accordance with Example 1 with 0.2% of dry extract of Ogon | 50 g |
| Gelled excipient | qsp 100 |

Use in daily local application to avoid the appearance of allergic reaction or to reduce the magnitude thereof.

EXAMPLE 10

Mascara for Sensitive Eyelids

| | |
|---|---|
| Composition of liposomes prepared in accordance with Example 2 with 0.15% of dry extract of Ogon | 20 g |
| Gelled oil-in-water emulsion laden with pigments | qsp 100 |

EXAMPLE 11

Composition for Masking Circles (around eyes) Intended for Sensitive Skins

| | |
|---|---|
| Composition of liposomes prepared in accordance with Example 1 with 0.2% dry extract of Ogon | 10 g |
| Oil-in-water emulsion laden with pigments | qsp 100 |

EXAMPLE 12

Foundation for Sensitive Skins

| | |
|---|---|
| Composition of liposomes prepared in accordance with Example 1 with 0.1% of dry extract of Ogon | 20 g |
| Oil-in-water emulsion laden with pigments | qsp 100 |

EXAMPLE 13

Anti-allergic and Anti-Inflammatory Composition

| | |
|---|---|
| Composition of liposomes prepared in accordance with Example 3 with 0.1% of baicaleine | 20 g |
| Oil-in-water emulsion | qsp 100 |

EXAMPLE 14

Day Cream for Delaying Ageing of the Skin

| | |
|---|---|
| Composition of liposome prepared in accordance with Example 1 with 0.3 of dry extract of Ogon | 20 g |
| Emulsified oil-in-water excipient | qsp 100 |

Daily application in the morning on those parts of the body exposed to daylight.

I claim:

1. A method for effecting a skin care treatment comprising topically applying to the skin a skin care efficient amount of hydrated lipidic lamellar phases or liposomes consisting essentially of an extract of Scutellaria as the active ingredient thereof, said extract being obtained by extraction with a solvent selected from the group consisting of a polar organic solvent, a polar water and organic solvent mixture, and an apolar organic solvent.

2. The method of claim 1, which is a method for treatment of an inflammatory skin condition.

3. The method of claim 1, which is a method for the treatment of an allergic skin condition.

4. The method of claim 1, which is a method for the care of sensitive skin.

5. The method of claim 1, which is a method for delaying aging of the skin.

6. The method of claim 1, wherein said hydrated lipidic lamellar phases or liposomes are present in a composition in an amount sufficient for providing a concentration in extract of Scutellaria ranging between 0.0001% and 2% by weight of the composition.

7. The method of claim 1, wherein the Scutellaria is selected from the group consisting of *Scutellaria baicalensis*, *Scutellaria viscidula* and *Scutellaria galericulata*.

8. The method of claim 7, wherein the Scutellaria extract is an extract of roots of Scutellaria.

9. The method of claim 1, wherein the Scutellaria extract is an extract of roots of *Scutellaria baicalensis georgi*.

10. The method of claim 9, wherein the extract of roots of *Scutellaria baicalensis georgi* is an extract obtained by extraction with 50% volume/volume water-ethanol solution.

11. The method of claim 1, wherein the hydrated lipidic lamellar phases or liposomes are present in a composition in an amount sufficient for having a concentration of Scutellaria extract ranging between 0,001 and 0.4% by weight of the composition.

* * * * *